(12) United States Patent
Kikuchi et al.

(10) Patent No.: US 12,019,005 B2
(45) Date of Patent: Jun. 25, 2024

(54) CELL OBSERVATION SYSTEM AND CELL OBSERVATION METHOD

(71) Applicants: NATIONAL UNIVERSITY CORPORATION HAMAMATSU UNIVERSITY SCHOOL OF MEDICINE, Hamamatsu (JP); HAMAMATSU PHOTONICS K.K., Hamamatsu (JP)

(72) Inventors: Hirotoshi Kikuchi, Hamamatsu (JP); Hidenao Yamada, Hamamatsu (JP); Amane Hirotsu, Hamamatsu (JP); Daisuke Yamashita, Hamamatsu (JP); Shigetoshi Okazaki, Hamamatsu (JP)

(73) Assignees: NATIONAL UNIVERSITY CORPORATION HAMAMATSU UNIVERSITY SCHOOL OF MEDICINE, Hamamatsu (JP); HAMAMATSU PHOTONICS K.K., Hamamatsu (JP)

( * ) Notice: Subject to any disclaimer, the term of this patent is extended or adjusted under 35 U.S.C. 154(b) by 491 days.

(21) Appl. No.: 17/310,813

(22) PCT Filed: Feb. 14, 2020

(86) PCT No.: PCT/JP2020/005846
§ 371 (c)(1),
(2) Date: Aug. 25, 2021

(87) PCT Pub. No.: WO2020/175189
PCT Pub. Date: Sep. 3, 2020

(65) Prior Publication Data
US 2022/0120660 A1    Apr. 21, 2022

(30) Foreign Application Priority Data
Feb. 27, 2019    (JP) .............................. 2019-033782

(51) Int. Cl.
*G01N 15/14*    (2024.01)
*G02B 21/36*    (2006.01)
(Continued)

(52) U.S. Cl.
CPC ....... *G01N 15/1425* (2013.01); *G02B 21/361* (2013.01); *G01N 2015/012* (2024.01);
(Continued)

(58) Field of Classification Search
CPC .......... G01N 15/1425; G01N 15/1475; G01N 2015/1454; G01N 15/1404;
(Continued)

(56) References Cited

U.S. PATENT DOCUMENTS 8,155,420 B2 *    4/2012    Meyer ................... G06T 7/0002
                                                         382/128
9,060,119 B2 *    6/2015    Ishii ..................... H04N 23/843
(Continued)

FOREIGN PATENT DOCUMENTS

JP    2001-255260 A    9/2001
JP    2005-021831 A    1/2005
(Continued)

OTHER PUBLICATIONS

Awatsuji, Yasuhiro et al., "Digital Holography : A Technique Capable of Three-Dimensional and High-Precision Measurement for Moving Object," Systems, Control and Information, 2008, vol. 52, No. 11, pp. 407-413, with partial English language translation.
(Continued)

*Primary Examiner* — Abdullahi Nur
(74) *Attorney, Agent, or Firm* — Faegre Drinker Biddle & Reath LLP

(57) ABSTRACT

A cell observation system observes a cell moving in a flow path with a fluid, and includes a first imaging apparatus, a second imaging apparatus, and a control device. The first
(Continued)

imaging apparatus includes a first optical system and a first imaging element, and captures an image of the cell at a first position in a moving direction. The second imaging apparatus includes a second optical system, in which a focus is adjusted based on a focus adjustment signal, and a second imaging element, and captures an image of the cell at a second position downstream of the first position. The control device obtains a passing position of the cell in a cross section of the flow path based on the image obtained by the first imaging element, generates the focus adjustment signal, and provides the signal to the second optical system.

14 Claims, 8 Drawing Sheets

(51) Int. Cl.
*G01N 15/01* (2024.01)
*G01N 15/1433* (2024.01)
*G01N 15/1434* (2024.01)

(52) U.S. Cl.
CPC ... *G01N 2015/016* (2024.01); *G01N 15/1433* (2024.01); *G01N 2015/144* (2013.01)

(58) Field of Classification Search
CPC ........... G01N 15/1434; G01N 15/1459; G02B 21/361; G02B 21/26
See application file for complete search history.

(56) References Cited

U.S. PATENT DOCUMENTS

| | | | |
|---|---|---|---|
| 2004/0217256 A1* | 11/2004 | Ortyn ................. | G01N 15/1459 250/201.4 |
| 2005/0085708 A1* | 4/2005 | Fauver ............... | G01N 21/4795 600/407 |
| 2009/0051898 A1* | 2/2009 | Hwang ................. | G01N 21/65 356/311 |
| 2010/0296713 A1* | 11/2010 | Meyer .................. | G06T 7/0002 382/224 |
| 2016/0291306 A1* | 10/2016 | Fukuda ................ | G02B 21/244 |
| 2017/0285000 A1* | 10/2017 | Fukuda ................ | G02B 21/367 |
| 2018/0267021 A1 | 9/2018 | Suresh et al. | |

FOREIGN PATENT DOCUMENTS

| | | |
|---|---|---|
| JP | 2015-510592 A | 4/2015 |
| WO | WO-2013/120886 A1 | 8/2013 |
| WO | WO 2014/146062 A2 | 9/2014 |
| WO | WO-2018/067770 A1 | 4/2018 |

OTHER PUBLICATIONS

Langehanenberg, Patrik et al., "Autofocusing in digital holographic phase contrast microscopy on pure phase objects for live cell imaging," Applied Optics, vol. 47, No. 19, Jul. 1, 2008, p. D176-p. D182.

Liebling, Michael et al., "Autofocus for digital Fresnel holograms by use of a Fresnelet-sparsity criterion," J. Opt. Soc. Am. A, vol. 21, No. 12, Dec. 2004, pp. 2424-2430.

Onuki, Ichiro, "Digital Camera with Phase Detection Image Sensor," The Journal of The Institute of Image Information and Television Engineers, Special Issue: The Latest Technologies about Digital Camera, 2014, vol. 68, No. 3, pp. 203-207, with partial English language translation.

Park, Yongkeun et al., "Fresnel particle tracing in three dimensions using diffraction phase microscopy," Optics Letters, 2007, Apr. 1, 2007, vol. 32, No. 7, pp. 811-813.

Rinehart, Matthew T. et al., "Influence of defocus on quantitative analysis of microscopic objects and individual cells with digital holography," Biomedical Optics Express, Jun. 1, 2015, vol. 6, No. 6, pp. 2067-2075.

Yamada, Hidenao et al., "Tomographic Phase Imaging Flow Cytometry for Detecting Circulating Tumor Cells," Medical Imaging Technology, Mar. 2016, vol. 34, No. 2, pp. 95-102.

Yamauchi, Toyohiko et al., "Miniaturization of quantitative phase microscope and various application measurements =desktop two-beam interference microscope without air surface plate=," Optical Alliance, Feb. 2017, p. 26-p. 29, with partial English language translation.

International Preliminary Report on Patentability dated Sep. 10, 2021 for PCT/JP2020/005846.

* cited by examiner

CELL OBSERVATION SYSTEM AND CELL OBSERVATION METHOD

TECHNICAL FIELD

The present disclosure relates to a cell observation system and a cell observation method.

BACKGROUND ART

In a cell observation system (flow cytometer or imaging flow cytometer) that observes a cell moving in a flow path with a fluid, focusing of an imaging apparatus is important to acquire a clear image of the cell being an observation object. By acquiring the clear image of the cell, for example, it is possible to identify whether or not the cell is a cancer cell (circulating tumor cell) included in a cancer patient.

The flow cytometer uses a point sensor type photodetector such as a photomultiplier tube and a photodiode. In the cell observation using the flow cytometer, cells are caused to flow at a flow speed of several m/s to 10 m/s.

The imaging flow cytometer uses a linear array sensor type or two-dimensional sensor type photodetector. In the cell observation using the imaging flow cytometer, it is said that cells are caused to flow at a flow speed of several mm/s to several 10 mm/s. This flow speed is about $1/10^3$ of that of the cell observation using the flow cytometer. The imaging flow cytometers include a two-dimensional imaging flow cytometer capable of acquiring a quantitative phase image of the cell, and a three-dimensional imaging flow cytometer capable of acquiring a three-dimensional image for a refractive index distribution of the cell.

In general, in the flow cytometer, the cells are caused to flow with the fluid such as a culture solution, and thus, by a hydrodynamic focusing effect, the cells can be substantially aligned along a flow direction. By the hydrodynamic focusing effect, even when the focus of the optical system of the imaging apparatus is fixed, it is possible to acquire the image of the cell in focus.

The degree of alignment of the cells by the hydrodynamic focusing effect depends on a volume ratio of a sample liquid (cell suspension) and a sheath liquid (culture solution). This volume ratio is, in general, controlled by a pressure applied to extrude these liquids. By reducing the volume ratio, a diameter of the sample liquid column is reduced, and as a result, the cells are more truly aligned. On the other hand, by increasing the volume ratio, the diameter Δd of the sample liquid column is increased, and as a result, the cells do not flow with true alignment. In this case, the cells flow over a range having a thickness in an optical axis direction of the optical system of the imaging apparatus, and the image of the cell not in focus is acquired.

On the other hand, when the diameter Δd of the sample liquid column is smaller than a depth of focus (DOF) of the optical system of the imaging apparatus (that is, DOF>Δd), the image of the cell in focus is obtained. Further, in the flow cytometer, when an adjustment of an instrument that affects a position of a sample nozzle is performed, a position of the cells flowing substantially in a line in the flow path cross section changes, and as a result, the image of the cell not in focus is acquired. Further, at the current technical level, a time required for the focus adjustment of the imaging optical system is in general said to be at least 1 μs, and a sufficient response speed cannot be obtained.

In order to avoid these two technical problems, a preliminary sample or a dummy sample such as a bead is caused to flow before the main measurement, the focus adjustment is performed to determine a focus plane, and then a test sample is caused to flow. When the cell flows in a time shorter than a time required for the focus adjustment of the imaging optical system, focus is not readjusted while the test sample is flowing.

In the imaging flow cytometer, a linear array sensor (including TDI sensor) is often used by using the movement of the cell of an imaging object. In the linear array sensor, the object is scanned in the flow direction for each line (L1, L2, L3, . . . ) in the direction perpendicular to the flow direction to acquire the image. When a spherical object such as the cell is imaged by scanning in the flow direction, it is necessary to estimate the focus of the entire cell on the first line (L1). However, this is difficult.

In the inventions described in Patent Documents 1 and 2, the imaging apparatus measures a focus deviation amount by an optical system provided separately from the imaging optical system, and adjusts the focus of the imaging optical system based on a measurement result. This imaging apparatus performs a measurement of the focus deviation amount and imaging at a common position in the moving direction of the cell in the flow path.

CITATION LIST

Patent Literature

Patent Document 1: US Patent Application Publication No. 2004/0217256
Patent Document 2: Japanese Patent Application Laid-Open Publication No. 2001-255260

Non Patent Literature

Non Patent Document 1: Y. Park et al., "Fresnel particle tracing in three dimensions using diffraction phase microscopy", Opt. Lett. Vol. 32, pp. 811-813, 2007
Non Patent Document 2: Toyohiko Yamauchi et al., "Miniaturization of quantitative phase microscope and various application measurements=desktop two-beam interference microscope without air surface plate=", Optical Alliance, pp. 26-29, 2017.2.
Non Patent Document 3: Hidenao Yamada et al., "Tomographic phase imaging flow cytometry for detecting circulating tumor cells", Medical Imaging Technology, Vol. 34 No. 2, pp. 95-102, 2016
Non Patent Document 4: P. Langehanenberg et al., "Autofocusing in digital holographic phase contrast microscopy on pure phase objects for live cell imaging", Appl. Opt. Vol. 47, pp. D176-D182, 2008
Non Patent Document 5: M. Liebling et al., "Autofocus for digital Fresnel holograms by use of a Fresnelet-sparsity criterion", J. Opt. Soc. Am. A. Vol. 21, pp. 2424-2430, 2004
Non Patent Document 6: M. T. Rinehart et al., "Influence of defocus on quantitative analysis of microscopic objects and individual cells with digital holography", Biomed. Opt. Express. Vol. 6, pp. 2067-2075, 2015
Non Patent Document 7: Ichiro Onuki, "Chapter 4 Camera using imaging plane phase difference sensor", The journal of the Institute of Image Information and Television Engineers Vol. 68, pp. 203-207, 2014

SUMMARY OF INVENTION

Technical Problem

In the inventions described in Patent Documents 1 and 2, a speed at which the cells flow in the flow path is restricted by a time required for the measurement of the focus deviation amount and the focus adjustment of the imaging optical system. Since there is no guarantee that the position of the next flowing cell in the optical axis direction is the same as that of the previous cell, in the above invention, the flow speed of the cell is restricted by the focusing speed (time required for the measurement of the focus deviation amount and the focus adjustment of the imaging optical system).

An object of an embodiment is to provide a cell observation system and a cell observation method capable of relaxing restriction of a flow speed of a cell due to a focusing speed.

Solution to Problem

An embodiment is a cell observation system. The cell observation system is a cell observation system for observing a cell moving in a flow path with a fluid, and includes (1) a first imaging apparatus including a first optical system and a first imaging element, and for capturing an image of the cell by receiving, by the first imaging element, light reaching the first imaging element from the cell at a first position in a moving direction of the cell in the flow path through the first optical system; (2) a second imaging apparatus including a second optical system, in which a focus is adjusted based on a focus adjustment signal, and a second imaging element, and for capturing an image of the cell by receiving, by the second imaging element, light reaching the second imaging element from the cell at a second position downstream of the first position in the moving direction of the cell in the flow path through the second optical system; and (3) a control device for obtaining a passing position of the cell in a cross section of the flow path based on the image obtained by imaging by the first imaging element of the first imaging apparatus, and generating the focus adjustment signal based on the obtained passing position to provide the signal to the second optical system of the second imaging apparatus.

An embodiment is a cell observation method. The cell observation method is a cell observation method for observing a cell moving in a flow path with a fluid, and includes (1) a first imaging step of, using a first imaging apparatus including a first optical system and a first imaging element, capturing an image of the cell by receiving, by the first imaging element, light reaching the first imaging element from the cell at a first position in a moving direction of the cell in the flow path through the first optical system; (2) a second imaging step of, using a second imaging apparatus including a second optical system, in which a focus is adjusted based on a focus adjustment signal, and a second imaging element, capturing an image of the cell by receiving, by the second imaging element, light reaching the second imaging element from the cell at a second position downstream of the first position in the moving direction of the cell in the flow path through the second optical system; and (3) a focus adjustment instruction step of, after the first imaging step and before the second imaging step, obtaining a passing position of the cell in a cross section of the flow path based on the image obtained by imaging by the first imaging element of the first imaging apparatus, and generating the focus adjustment signal based on the obtained passing position to provide the signal to the second optical system of the second imaging apparatus.

Advantageous Effects of Invention

According to the cell observation system and the cell observation method of the embodiments, restriction of a flow speed of a cell due to a focusing speed can be relaxed.

DESCRIPTION OF EMBODIMENTS

Hereinafter, embodiments of a cell observation system and a cell observation method will be described in detail with reference to the accompanying drawings. In the description of the drawings, the same elements will be denoted by the same reference signs, and redundant description will be omitted. The present invention is not limited to these examples.

Figure 1:
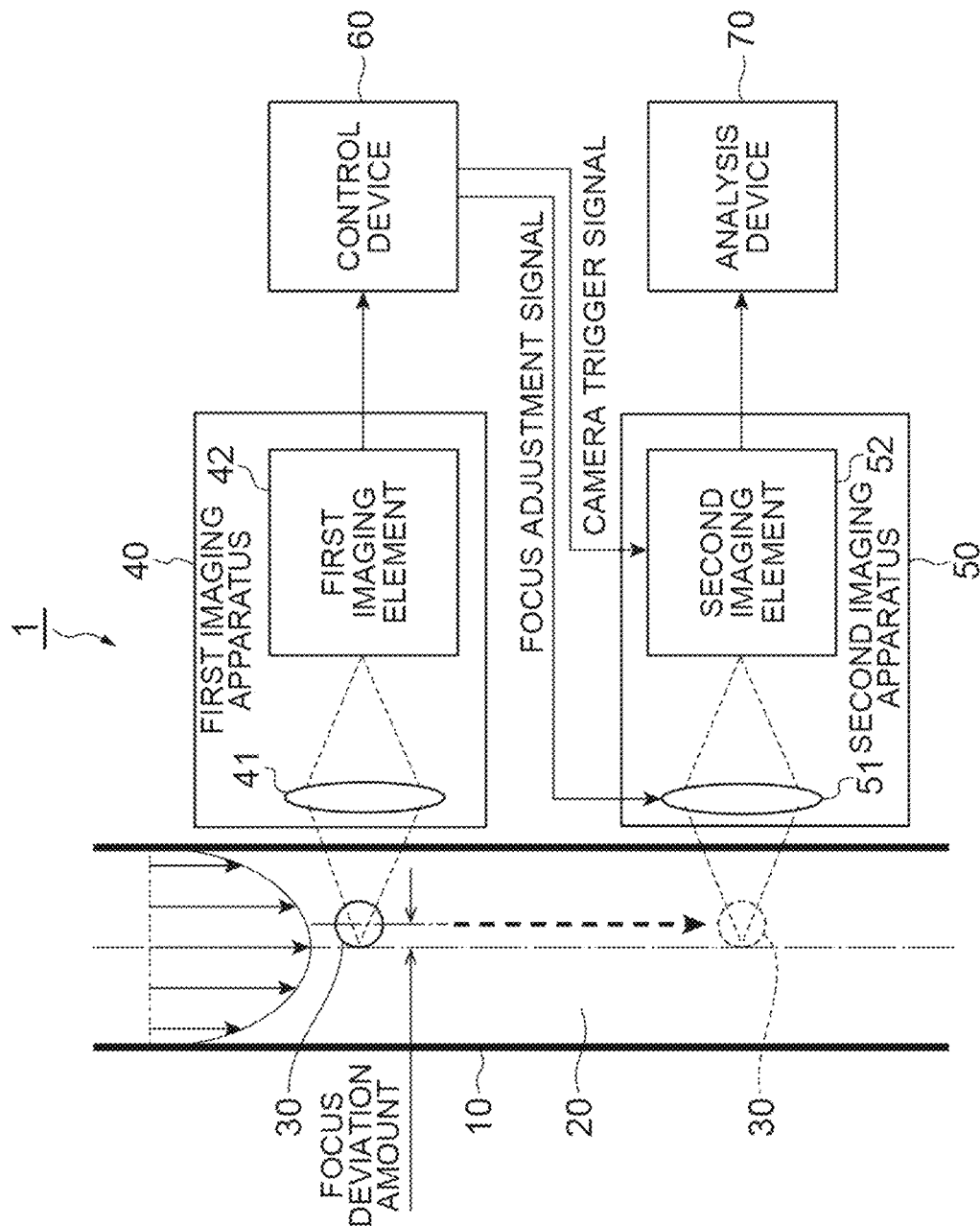
FIG. 1 is a diagram illustrating a configuration of a cell observation system.

FIG. 1 is a diagram illustrating a configuration of a cell observation system 1. The cell observation system 1 observes a cell 30 moving in a flow path 10 with a fluid 20. The cell observation system 1 includes a first imaging apparatus 40, a second imaging apparatus 50, a control device 60, and an analysis device 70.

For example, the flow path 10 is a flow cell, the fluid 20 is a culture solution, and the cell 30 is a red blood cell, a white blood cell, a CTC, or the like. The cell 30 is prepared in a state of being suspended in the culture solution. A suspension concentration is, for example, $10^6$ cells/mL. The cell suspension is guided to the flow path 10. The cell 30 is caused to move substantially on a straight line in the flow path 10 by the hydrodynamic focusing effect.

The first imaging apparatus 40 includes a first optical system 41 and a first imaging element 42. The first optical system 41 guides light reaching from the cell 30 at a first position in a moving direction of the cell 30 in the flow path 10 to a light receiving plane of the first imaging element 42. The first imaging element 42 is optically coupled to the first optical system 41, and captures an image of the cell 30 by receiving the light reaching the light receiving plane (first imaging step).

The second imaging apparatus 50 includes a second optical system 51 and a second imaging element 52. The second optical system 51 guides light reaching from the cell 30 at a second position in the moving direction of the cell 30 in the flow path 10 to a light receiving plane of the second imaging element 52. The second imaging element 52 is optically coupled to the second optical system 51, and captures an image of the cell 30 by receiving the light reaching the light receiving plane (second imaging step). The second position is downstream of the first position.

The second optical system 51 adjusts the focus based on a focus adjustment signal provided from the control device 60. After the focus adjustment, the second imaging element 52 captures the image of the cell 30, thereby acquiring a clear image of the cell 30 in focus. The imaging operation by the second imaging element 52 may be performed at a timing instructed by a camera trigger signal provided from the control device 60, or may be continuously performed with a constant frame rate.

The control device 60 is electrically coupled to the first imaging element 42 of the first imaging apparatus 40, and is electrically coupled to the second optical system 51 and the second imaging element 52 of the second imaging apparatus 50. The control device 60 inputs the image obtained by imaging by the first imaging element 42, and analyzes the image to obtain a passing position of the cell 30 in a cross section of the flow path 10. Further, the control device 60 generates the focus adjustment signal based on the obtained passing position, and provides the focus adjustment signal to the second optical system 51 (focus adjustment instruction step). Further, the control device 60 provides the camera trigger signal for instructing the timing of imaging by the second imaging element 52 to the second imaging element 52.

The control device 60 may be a general-purpose computer including a central processing unit (CPU) as a processor, a random access memory (RAM) or a read only memory (ROM) as a storage medium, an input unit such as a keyboard or a mouse, a display unit such as a liquid crystal display, and an input-output module. The control device 60 may be configured as a dedicated device using, for example, a microcomputer or a field programmable gate array (FPGA).

The analysis device 70 is electrically coupled to the second imaging element 52 of the second imaging apparatus 50. The analysis device 70 inputs the image obtained by imaging by the second imaging element 52, and analyzes the image to identify the type of the cell 30 in the image. The analysis device 70 may be a general-purpose computer including a CPU as a processor, a RAM or a ROM as a storage medium, an input unit such as a keyboard or a mouse, a display unit such as a liquid crystal display, and an input-output module.

The flow path 10 has a pipe structure made of a transparent material such as a glass, and the cell 30 is caused to flow therein with the fluid 20. The fluid 20 is, for example, a cell culture solution. In the imaging position (first position, second position), the wall surface of the flow path 10 is preferably flat, and the cross sectional shape of the flow path 10 is preferably rectangular (including square). In this way, it is possible to acquire the image for the cell with small distortion.

When the fluid 20 is caused to flow in the flow path 10, the fluid 20 is preferably caused to flow under a laminar flow condition. When a turbulent flow condition is used instead of the laminar flow condition, a flow line of the fluid 20 such as a culture solution does not fall within a plane perpendicular to the optical axis in many cases, and therefore, a position in the optical axis direction is different in the imaging position (first position, second position) of the cell 30 flowing along the flow line, and thus, an effect of the focus adjustment is not easily exhibited.

When the fluid 20 is caused to flow in the flow path 10, it is preferable to focus the cell 30 on a certain region (for example, a region near the center) in the cross section of the flow path 10 in advance upstream of the imaging position (first position, second position). As a method of realizing the focusing, hydrodynamic focusing, acoustic focusing, inertial focusing, and the like are known. By focusing the cell 30 near the center of the flow path 10 in advance in this way, the focus deviation amount can be restricted to a certain width ($\Delta d$).

The cell observation method of the present embodiment is to observe the cell 30 moving in the flow path 10 with the fluid 20 by using the first imaging apparatus 40 and the second imaging apparatus 50 described above.

In the first imaging step, the first imaging apparatus 40 including the first optical system 41 and the first imaging element 42 is used to capture the image of the cell by receiving, by the first imaging element 42, light reaching the first imaging element 42 from the cell 30 at a first position in the moving direction of the cell 30 in the flow path 10 through the first optical system 41. The image data obtained by the imaging is sent to the control device 60.

In the second imaging step, the second imaging apparatus 50 including the second optical system 51, in which the focus is adjusted based on the focus adjustment signal, and the second imaging element 52 is used to capture the image of the cell by receiving, by the second imaging element 52, light reaching the second imaging element 52 from the cell 30 at a second position downstream of the first position through the second optical system 51. The image of the cell obtained by the imaging is analyzed by the analysis device 70 to identify the type of the cell, and is displayed on the display unit.

In the focus adjustment instruction step after the first imaging step and before the second imaging step, the control device 60 obtains the passing position of the cell 30 in the cross section of the flow path 10 based on the image obtained by imaging by the first imaging element 42 of the first imaging apparatus 40. Then, the focus adjustment signal is generated based on the obtained passing position and provided to the second optical system 51 of the second imaging apparatus 50.

Figure 2:
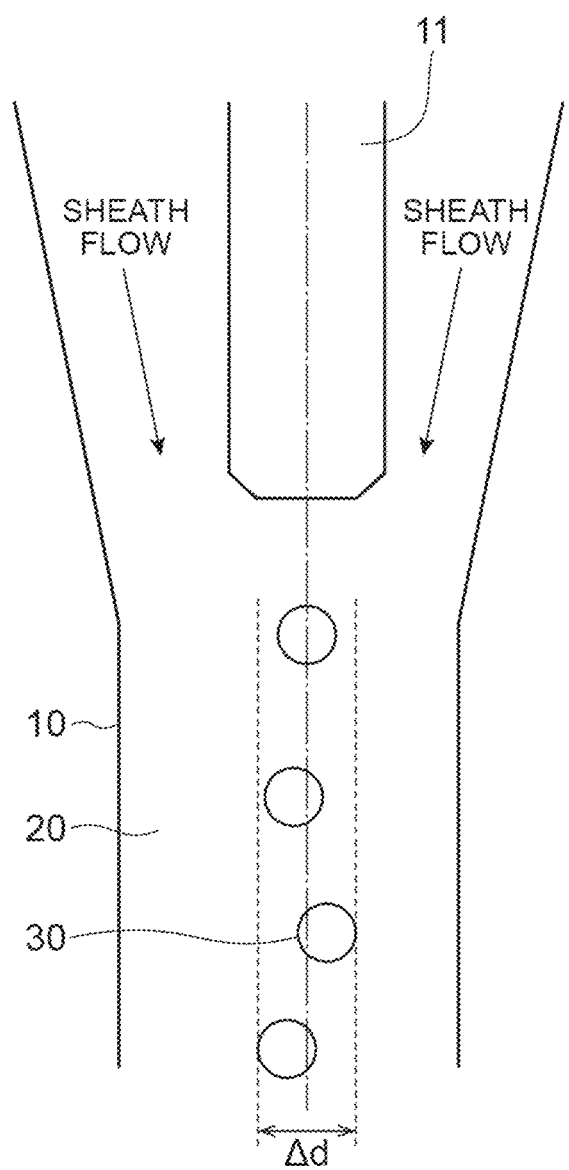
FIG. 2 is a diagram illustrating an example of a structure of a flow path.

FIG. 2 is a diagram illustrating an example of a structure of the flow path 10. In this structure, the fluid 20 is caused to flow as a laminar flow in the flow path 10 by utilizing the hydrodynamic focusing effect. A nozzle 11 is inserted into the flow path 10 upstream of the imaging position (first position, second position). The cell suspension (sample liquid) is supplied to the flow path 10 from the nozzle 11, and the sheath liquid is supplied to the flow path 10 from a concentric tube around the nozzle 11.

The flow rate can be adjusted by the pressure applied to each of the sample liquid and the sheath liquid, and the cell 30 contained in the sample liquid can be focused around the center of the flow path 10. When the flow rate of the sample liquid is Qsa and the flow rate of the sheath liquid is Qsh, the focusing width $\Delta d$ depends on the flow rate ratio (Qsh/Qsa) of the two liquids. Further, the average flow speed V of the cell 30 is determined by the flow paths of the two liquids, and is expressed by $V=(Qsh+Qsa)/S$, where S is the flow path cross sectional area. For example, when Qsh=30 µL/min, Qsa=2 µL/min, and $S=0.25^2$ mm², the average flow speed V is 8.5 mm/s.

The initial cell suspension concentration before being supplied from the nozzle 11 is, in general, $1\times10^6$ cells/mL. The volume fraction in this case is about 0.1%, and the presence of the cell 30 in the cell suspension is extremely sparse. Therefore, even when the cell concentration is locally increased by focusing the cell 30 near the center of the flow path 10, the distance between the cells 30 is sufficiently larger than the size of the cell 30 (in general, about 10 μm).

Figure 3:
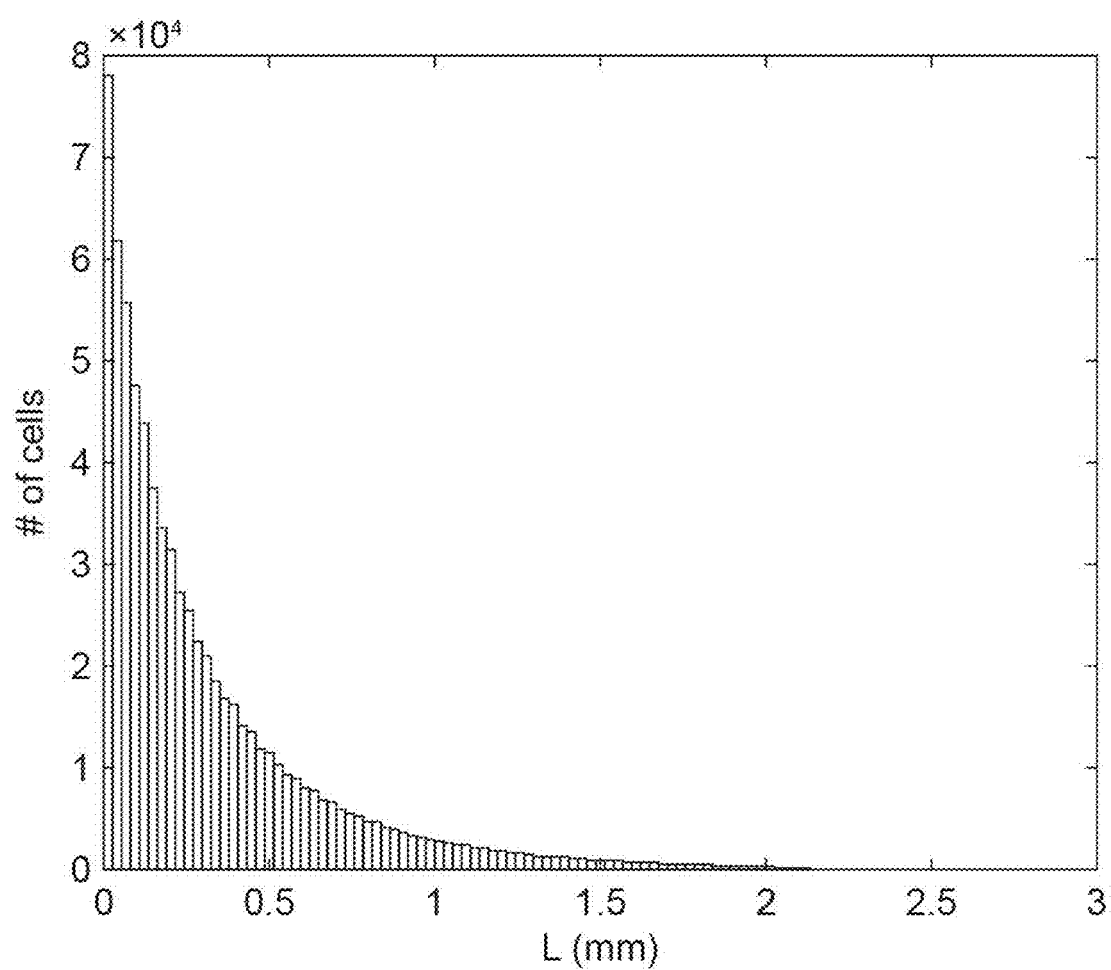
FIG. 3 is an example of a histogram of a distance between cells.

FIG. 3 shows an example of a histogram of the distance L between the cells 30. This histogram is obtained under the conditions of the above flow speed and the cell suspension concentration using the hydrodynamic focusing effect. In this example, the average distance between the cells 30 is 320 μm.

Figure 4:
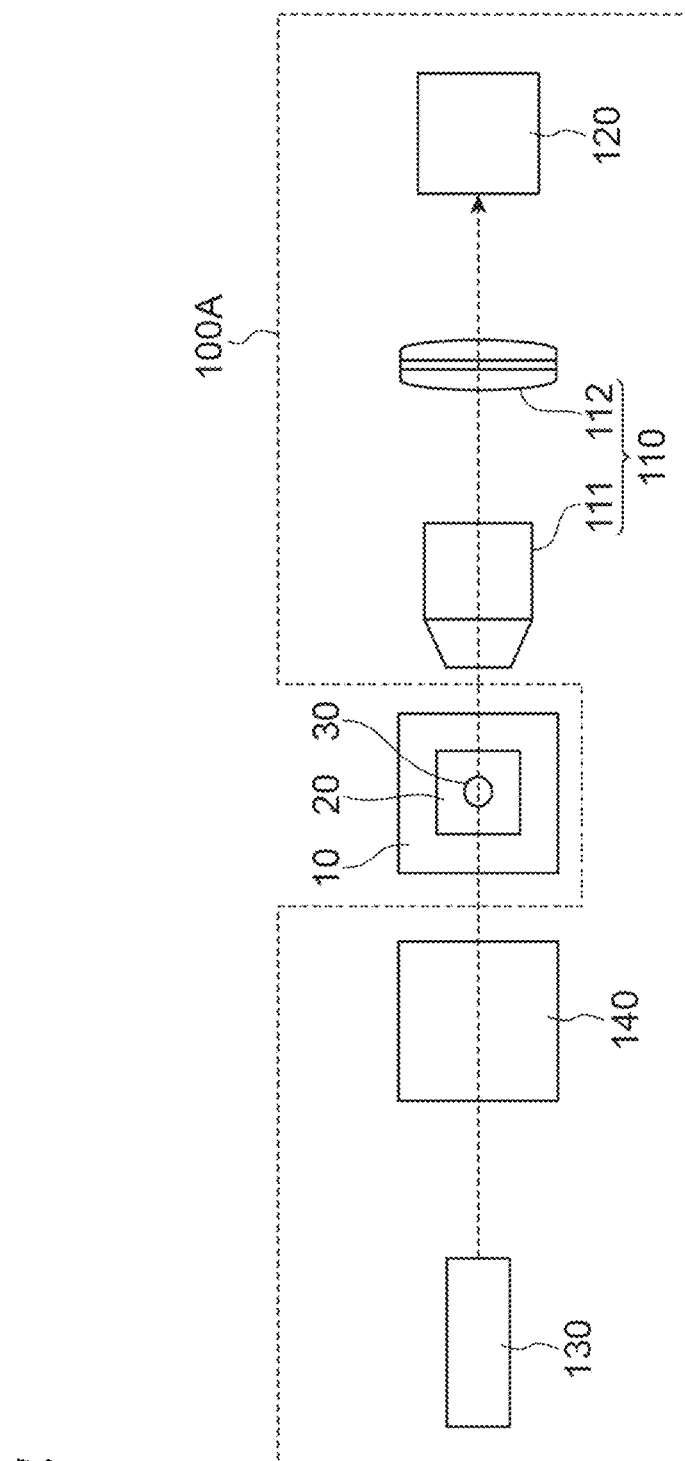
FIG. 4 is a diagram illustrating a configuration of an imaging apparatus.

FIG. 4 is a diagram illustrating a configuration of an imaging apparatus 100A. The imaging apparatus 100A is a configuration having a trans-illumination optical system, and can be used as the first imaging apparatus 40. The imaging apparatus 100A includes an imaging optical system 110 including an objective lens 111 and an imaging lens 112, an imaging element 120, a light source 130, and an irradiation optical system 140.

The light source 130 outputs light with which the cell 30 is irradiated. The light source 130 may be a laser light source (for example, a HeNe laser light source). The irradiation optical system 140 is optically coupled to the light source 130, and irradiates the cell 30 in the flow path 10 with the light output from the light source 130.

The irradiation optical system 140 is preferably a beam forming optical system that irradiates the cell 30 with line-shaped light having a beam cross section long in the vertical direction with respect to the moving direction of the cell 30 in the flow path 10, in terms of light energy efficiency. Further, when the cell 30 is irradiated with the line-shaped light, a linear array sensor can be used as the imaging element 120, and the exposure time of the linear array sensor can be shortened, so that the clear image can be acquired also for the cell 30 flowing faster.

The irradiation optical system 140 may be configured to include a focusing lens, a single mode optical fiber, a collimator lens, and a cylindrical lens to irradiate the cell 30 with the line-shaped light. In this case, the light output from the light source 130 is focused on an input end of the optical fiber by the focusing lens, and guided by the optical fiber. The guided light is output from an output end of the optical fiber, and converted into parallel light by the collimator lens provided at the output end. Then, the parallel light is focused only in one axis direction by the cylindrical lens, thereby forming the line-shaped beam near the cell focus.

The imaging optical system 110 corresponds to the first optical system 41 of the first imaging apparatus 40, and includes the objective lens 111 and the imaging lens 112. The objective lens 111 and the imaging lens 112 guide light from the cell 30 to the light receiving plane of the imaging element 120. For example, the magnification of the objective lens 111 is 20×, the NA of the objective lens 111 is 0.45, and the focal length of the imaging lens 112 is 200 mm. A position of the objective lens 111 in the optical axis direction is adjusted, and a focus is set to the center of the flow path 10. The imaging optical system 110 becomes a fixed focus.

The imaging element 120 corresponds to the first imaging element 42 of the first imaging apparatus 40. The imaging element 120 may be a linear array sensor. For example, a line sensor (model number raL2048-80 km) manufactured by Basler is preferably used as the imaging element 120. The size of one pixel of the line sensor is 7×7 μm. The imaging element 120 may continuously perform an imaging operation at a predetermined line rate.

The control device 60 obtains the focus deviation amount (deviation amount of the passing position of the cell 30 with respect to the reference position in the cross section of the flow path 10) as follows, based on the image acquired by the imaging apparatus 100A as the first imaging apparatus 40. The control device 60 creates a two-dimensional image by arranging one-dimensional images output one after another from the imaging element 120 being the line sensor in that order. For example, the two-dimensional image (M rows and N columns) can be obtained by arranging the M one-dimensional images (1 row and N columns). As long as the output of the one-dimensional image continues from the imaging element 120, the number of pixels of the two-dimensional image is increasing, and in addition, when a FIFO (first-in first-out) memory is used, old image data can be erased, and the latest two-dimensional image having a predetermined number of pixels can be stored.

The control device 60 detects whether or not there is a partial image indicating a desired cell in the two-dimensional image, and cuts out the partial image indicating the cell. In this case, whether or not there is the partial image indicating the desired cell is detected based on whether or not an intensity of each pixel exceeds a threshold value. Then, a rectangular image including the partial image indicating the cell is cut out.

The control device 60 obtains the deviation amount $\Delta Z$ of the cell 30 from the focus plane (conjugate plane with respect to the light receiving plane of the imaging element 120) of the imaging optical system 110 based on the rectangular image by a phase difference autofocus technique, an image plane phase difference focus technique, or an autofocus technique using digital holography. Since the rectangular image is blurred according to the deviation amount $\Delta Z$, the deviation amount $\Delta Z$ can be obtained from the blur amount (see Non Patent Document 1). The deviation amount $\Delta Z$ can take positive and negative values. The control device 60 generates the focus adjustment signal based on the deviation amount $\Delta Z$, and provides the focus adjustment signal to the second optical system 51 of the second imaging apparatus 50.

The control device 60 may determine whether to adjust the focus of the second optical system 51 based on the passing position (deviation amount $\Delta Z$) of the cell, and provide the focus adjustment signal to the second imaging apparatus 50 when it is determined that the focus of the second optical system 51 is to be adjusted. For example, when the depth of focus of the second optical system 51 is large and the deviation amount $\Delta Z$ is small, the control device 60 may not provide the focus adjustment signal to the second imaging apparatus 50. Further, when the deviation amount $\Delta Z$ of the cell with which the image is to be captured this time is the same as the deviation amount of the cell with which the image was captured last time, it is not necessary to move the focus position of the second optical system 51, and thus, the control device 60 may not provide the focus adjustment signal to the second imaging apparatus 50.

The second imaging apparatus 50 can also have substantially the same configuration as the imaging apparatus 100A. In addition, when the imaging apparatus 100A is used as the second imaging apparatus 50, it is preferable that the irradiation optical system 140 irradiates the cell 30 with light not in a line shape but in a plane shape, and it is preferable that the imaging element 120 is a two-dimensional array sensor. Further, the imaging optical system 110 may adjust the focus in response to the focus adjustment signal provided from the control device 60. At this time, it is preferable to move the objective lens 111 in the optical axis direction according to the deviation amount $\Delta Z$. As a result, the imaging optical system 110 is focused, and the clear image of the cell 30 in focus is acquired by the imaging element 120.

When the imaging apparatus 100A is used as the second imaging apparatus 50, the imaging element 120 may continuously perform imaging at a constant frame rate regardless of the focus adjustment operation of the imaging optical system 110. Further, the imaging element 120 may perform imaging at a timing instructed by the camera trigger signal provided from the control device 60.

Figure 5:
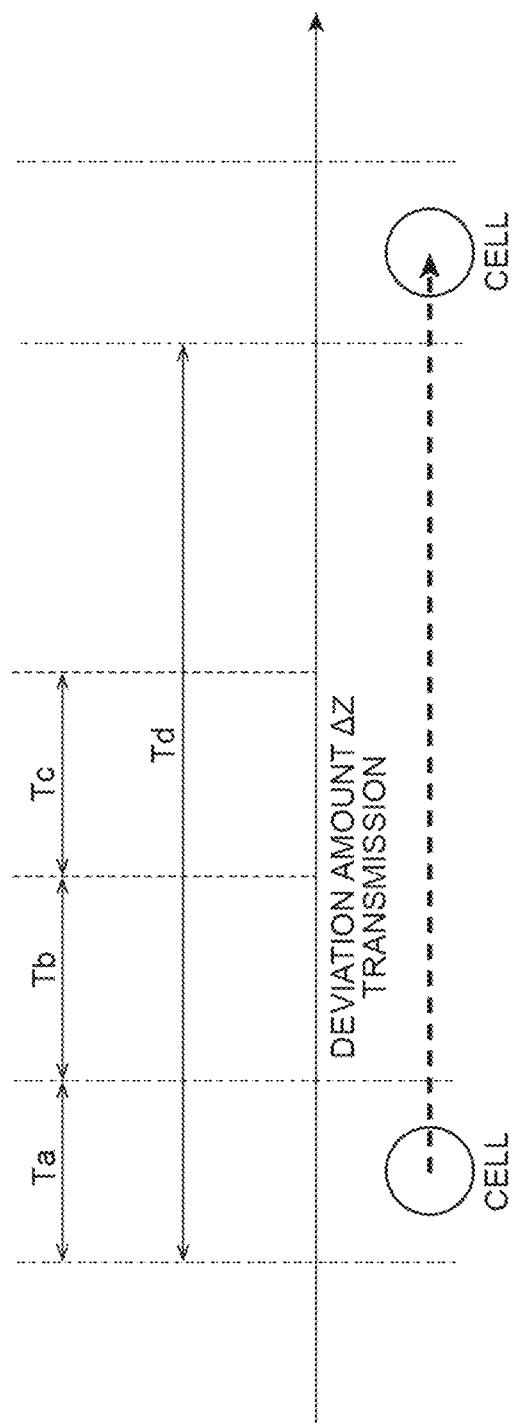
FIG. 5 is a timing chart when an imaging element performs imaging at a timing instructed by a camera trigger signal provided from a control device.

FIG. 5 is a timing chart when the imaging element 120 performs imaging at a timing instructed by the camera trigger signal provided from the control device 60. The distance along the cell moving direction between the first position where the first imaging apparatus 40 captures the image of the cell and the second position where the second imaging apparatus 50 captures the image of the cell is set to L. The average flow speed of the cell is set to V. A time difference Td between imaging by the first imaging apparatus 40 and imaging by the second imaging apparatus 50 is expressed by Td=L/V. The time required for imaging and sending image data in the first imaging apparatus 40 is set to Ta. The time required for calculating the deviation amount ΔZ based on the image data and generating the focus adjustment signal in the control device 60 (time required for the measurement of the focus deviation amount) is set to Tb.

The control device 60 outputs the focus adjustment signal to the second imaging apparatus 50 after the lapse of time (Ta+Tb) from the time when the first imaging apparatus 40 captures the image of the cell. Further, the control device 60 outputs the camera trigger signal to the second imaging apparatus 50 after the lapse of time (Td−Ta−Tb) from the time when the focus adjustment signal is output in consideration of the time Tc required for the focus adjustment in the second optical system 51 of the second imaging apparatus 50. There is a relationship of Ta+Tb+Tc<Td in these parameters.

Each of the first imaging apparatus 40 and the second imaging apparatus 50 may have various configurations in addition to the configuration having the trans-illumination optical system shown in FIG. 4. Each of the first imaging apparatus 40 and the second imaging apparatus 50 may be a configuration having an epi-illumination optical system. The first imaging apparatus 40 may be a configuration having an interference optical system such as a Mach-Zehnder interferometer, a Michelson interferometer, or the like (for example, a quantitative phase microscope (see Non Patent Document 2)). The second imaging apparatus 50 may be a quantitative phase microscope or a phase tomographic microscope (see Non Patent Document 3). The first imaging apparatus 40 may be a quantitative phase microscope, and the second imaging apparatus 50 may be a phase tomographic microscope.

As modifications of the imaging apparatus 100A, an imaging apparatus 100B (FIG. 6) having an epi-illumination optical system, an imaging apparatus 100C (FIG. 7) having an interference optical system, and an imaging apparatus 100D (FIG. 8) having a separator lens as the imaging lens in the imaging optical system will be described below.

Figure 6:
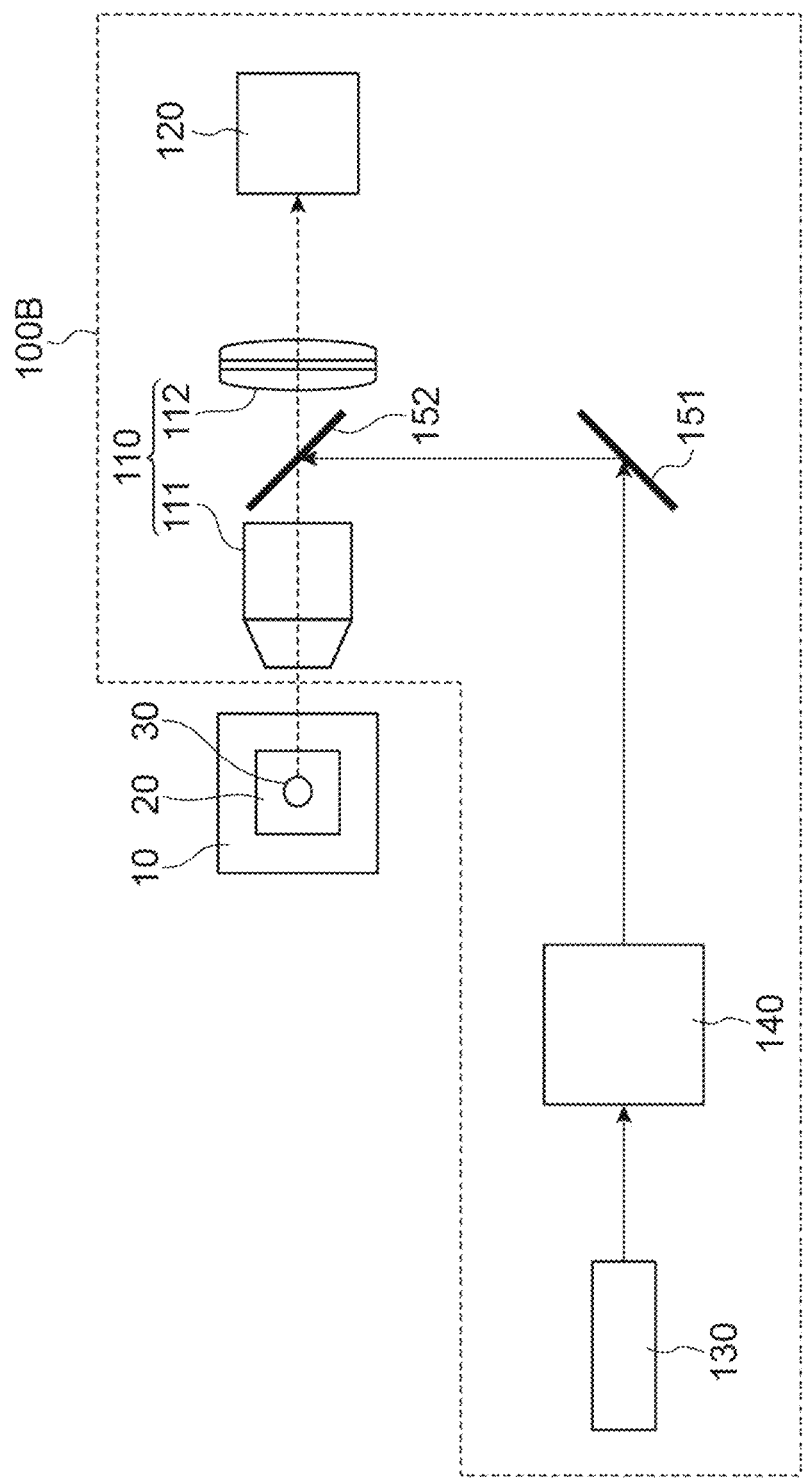
FIG. 6 is a diagram illustrating a configuration of the imaging apparatus.

FIG. 6 is a diagram illustrating a configuration of the imaging apparatus 100B. The imaging apparatus 100B is a configuration having an epi-illumination optical system, and includes the imaging optical system 110 including the objective lens 111 and the imaging lens 112, the imaging element 120, the light source 130, and the irradiation optical system 140, and further includes a mirror 151 and a beam splitter 152.

The mirror 151 reflects the light output from the light source 130 and beam-formed by the irradiation optical system 140 to the beam splitter 152. The beam splitter 152 is provided on an optical path between the objective lens 111 and the imaging lens 112. The beam splitter 152 reflects a part of the light reaching from the mirror 151 and inputs it to the objective lens 111, and transmits a part of the light reaching from the objective lens 111 and inputs it to the imaging lens 112. In this case, a dark field illumination image of the cell can be acquired.

A dichroic mirror that reflects excitation light and transmits fluorescence may be provided instead of the beam splitter 152. The light source 130 outputs the excitation light, and the fluorescence is generated from the cell irradiated with the excitation light. The dichroic mirror reflects the excitation light reaching from the mirror 151 and inputs it to the objective lens 111, and transmits the fluorescence reaching from the objective lens 111 and inputs it to the imaging lens 112. In this case, a fluorescence image of the cell can be acquired.

Figure 7:
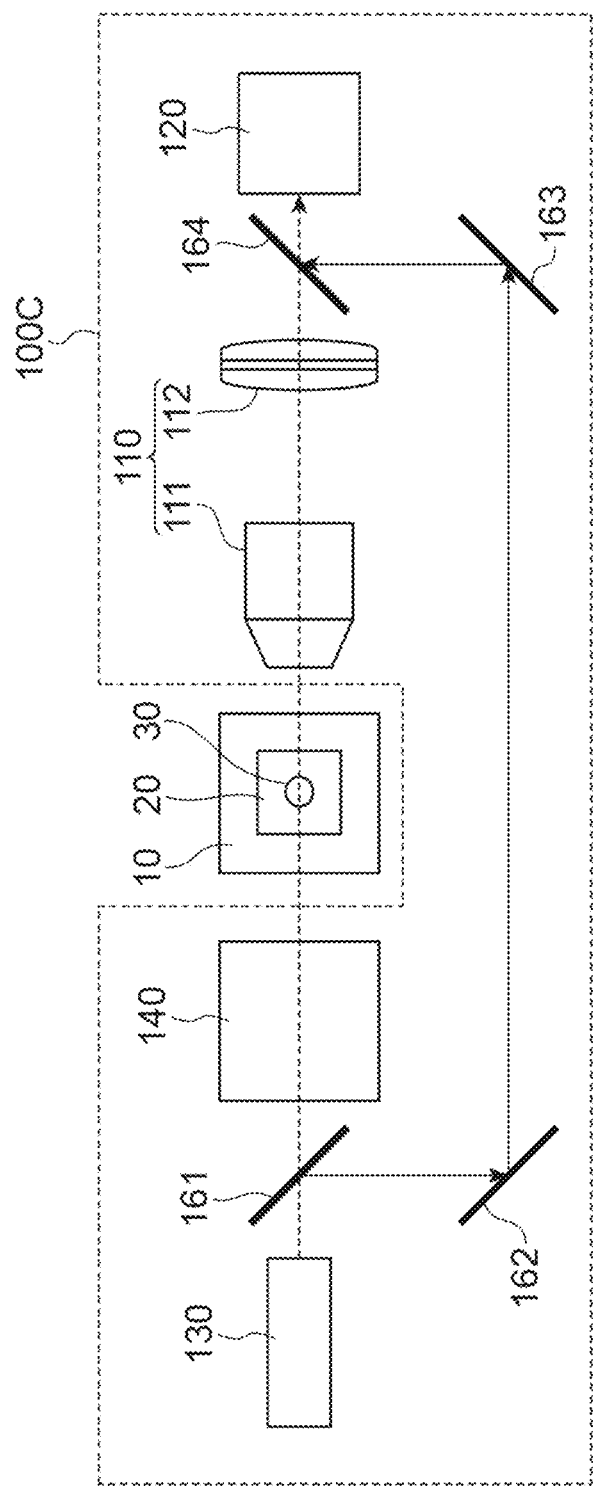
FIG. 7 is a diagram illustrating a configuration of the imaging apparatus.

FIG. 7 is a diagram illustrating a configuration of the imaging apparatus 100C. The imaging apparatus 100C is a configuration having an interference optical system, and includes the imaging optical system 110 including the objective lens 111 and the imaging lens 112, the imaging element 120, the light source 130, and the irradiation optical system 140, and further includes a beam splitter 161, a mirror 162, a mirror 163, and a beam splitter 164.

The beam splitter 161 is provided on an optical path between the light source 130 and the irradiation optical system 140. The beam splitter 161 inputs the light output from the light source 130, reflects a part of the light, and transmits the remaining part, thereby splitting the light into two beams. The irradiation optical system 140 inputs the light transmitted through the beam splitter 161.

The beam splitter 164 is provided on an optical path between the imaging lens 112 and the imaging element 120. The beam splitter 164 inputs the light reaching from the imaging lens 112, inputs the light reaching after being reflected by the beam splitter 161 and further reflected by the mirrors 162, 163, combines the light beams, and outputs the light to the imaging element 120.

The optical system from the beam splitter 161 to the beam splitter 164 constitutes a Mach-Zehnder interferometer. The imaging element 120 can acquire an interference image of the cell. Further, a phase image of the cell can be acquired by changing the optical path difference between the two optical paths from the beam splitter 161 to the beam splitter 164, acquiring the interference image at each optical path difference, and analyzing the plurality of interference images.

In addition, the optical system illustrated in this diagram is a Mach-Zehnder interferometer, but may be an optical system of a Michelson interferometer.

In the configuration examples described above, when the imaging apparatus 100A, 100B, or 100C is used as the first imaging apparatus 40, the imaging element 120 may be a linear array sensor in which pixels are arrayed one-dimensionally, or may be a two-dimensional array sensor in which pixels are arrayed two-dimensionally. In the latter case, the cross sectional shape of the light output from the irradiation optical system 140 is not a line shape, but a circular shape, quadrangular shape, or the like.

When the imaging apparatus 100A, 100B or 100C is used as the second imaging apparatus 50, the imaging element 120 may be a linear array sensor in which pixels are arrayed one-dimensionally, or may be a two-dimensional array sensor in which pixels are arrayed two-dimensionally. In the former case, the cross sectional shape of the light output from the irradiation optical system 140 is preferably a line shape.

Further, the control device 60 may perform digital refocusing processing (see Non Patent Documents 4 to 6) on the image of the cell acquired by the first imaging apparatus 40, determine whether to perform imaging by the second imaging apparatus 50 based on the image in focus, and provide the camera trigger signal to the second imaging apparatus 50 when it is determined to perform imaging by the second imaging apparatus 50.

As a method of autofocus (AF), contrast AF, phase difference AF, and image plane phase difference AF are well known (Non Patent Document 7). In these, the contrast AF is not suitable for use in the present embodiment because it includes mechanical driving to move the lens back and forth. On the other hand, the phase difference AF and the image plane phase difference AF do not require mechanical driving of the lens, and the deviation amount ΔZ and its direction (positive or negative of ΔZ) can be known, and therefore can be suitably used in the present embodiment.

Figure 8:
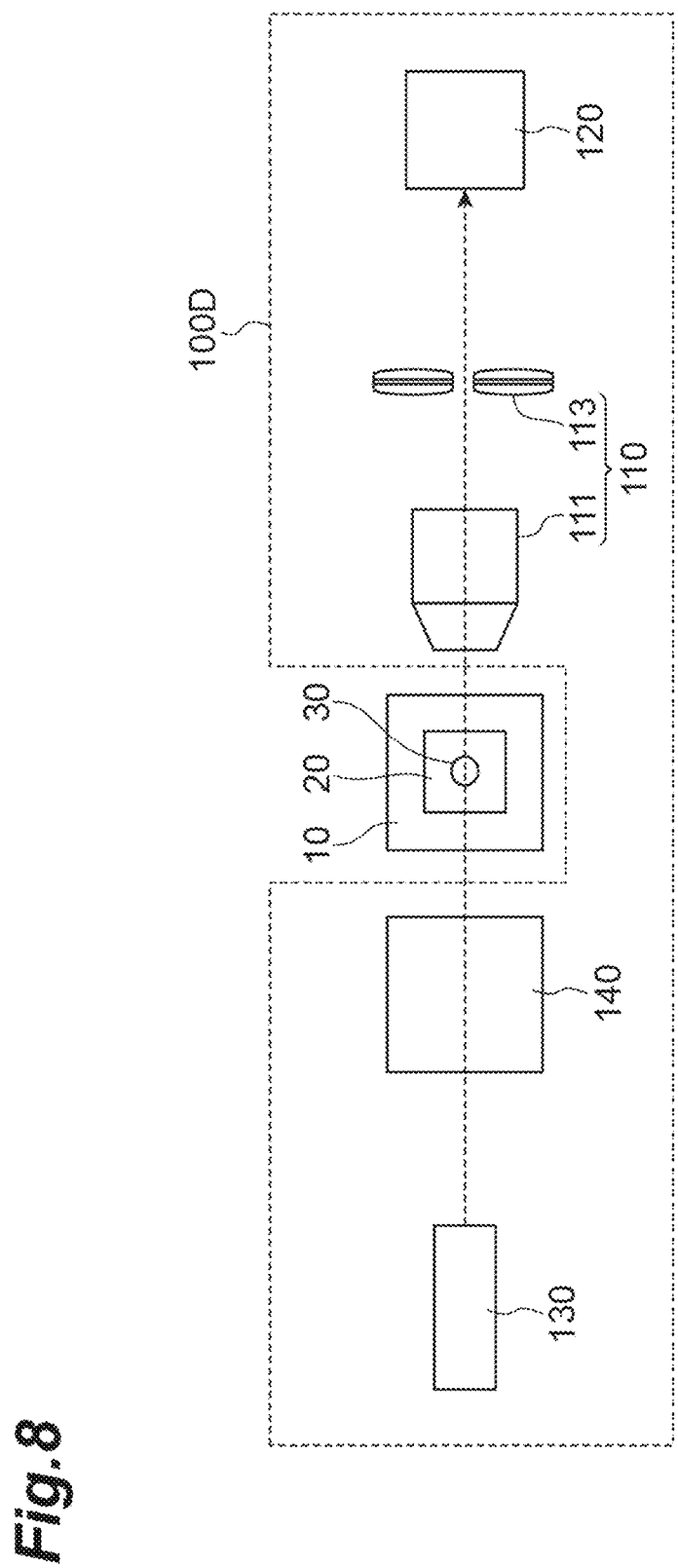
FIG. 8 is a diagram illustrating a configuration of the imaging apparatus.

In the configuration illustrated in FIG. 8, the deviation amount ΔZ can be obtained by the phase difference AF. FIG. 8 is a diagram illustrating a configuration of the imaging apparatus 100D. The imaging apparatus 100D is different from the imaging apparatus 100A of the configuration having the trans-illumination optical system illustrated in FIG. 4 in that the imaging optical system 110 includes a separator lens 113 as the imaging lens.

In this configuration, the above-described digital refocusing processing cannot be performed. Therefore, it cannot be determined whether to perform imaging by the second imaging apparatus 50 based on the image of the cell acquired by the first imaging apparatus 40, and the camera trigger signal cannot be provided to the second imaging apparatus 50.

In the present embodiment, by relaxing restriction of the flow speed of the cell due to the focusing speed, it is possible to acquire a clear (small blur) image of the cell even when the cell is moving at high speed. Therefore, it is possible to improve the throughput of the inspection of the cell flowing in the flow path. Even when the fluid flow in the flow path is not a complete laminar flow and the cell moves spatially randomly, a clear (small blur) image of the cell can be acquired.

A line sensor can be used as the imaging element in both or one of the first imaging apparatus and the second imaging apparatus, and in this case, the system can be configured at low cost compared to the case where a two-dimensional sensor is used as the imaging element in both of the first imaging apparatus and the second imaging apparatus.

The cell observation system and the cell observation method are not limited to the embodiments and configuration examples described above, and various other modifications are possible.

The cell observation system of the above embodiment is a cell observation system for observing a cell moving in a flow path with a fluid, and includes (1) a first imaging apparatus including a first optical system and a first imaging element, and for capturing an image of the cell by receiving, by the first imaging element, light reaching the first imaging element from the cell at a first position in a moving direction of the cell in the flow path through the first optical system; (2) a second imaging apparatus including a second optical system, in which a focus is adjusted based on a focus adjustment signal, and a second imaging element, and for capturing an image of the cell by receiving, by the second imaging element, light reaching the second imaging element from the cell at a second position downstream of the first position in the moving direction of the cell in the flow path through the second optical system; and (3) a control device for obtaining a passing position of the cell in a cross section of the flow path based on the image obtained by imaging by the first imaging element of the first imaging apparatus, and generating the focus adjustment signal based on the obtained passing position to provide the signal to the second optical system of the second imaging apparatus.

The cell observation method of the above embodiment is a cell observation method for observing a cell moving in a flow path with a fluid, and includes (1) a first imaging step of, using a first imaging apparatus including a first optical system and a first imaging element, capturing an image of the cell by receiving, by the first imaging element, light reaching the first imaging element from the cell at a first position in a moving direction of the cell in the flow path through the first optical system; (2) a second imaging step of, using a second imaging apparatus including a second optical system, in which a focus is adjusted based on a focus adjustment signal, and a second imaging element, capturing an image of the cell by receiving, by the second imaging element, light reaching the second imaging element from the cell at a second position downstream of the first position in the moving direction of the cell in the flow path through the second optical system; and (3) a focus adjustment instruction step of, after the first imaging step and before the second imaging step, obtaining a passing position of the cell in a cross section of the flow path based on the image obtained by imaging by the first imaging element of the first imaging apparatus, and generating the focus adjustment signal based on the obtained passing position to provide the signal to the second optical system of the second imaging apparatus.

In the above cell observation system, the control device may determine whether to adjust the focus of the second optical system based on the passing position, and may provide the focus adjustment signal to the second imaging apparatus when it is determined to adjust the focus of the second optical system. Further, in the above cell observation method, in the focus adjustment instruction step, whether to adjust the focus of the second optical system may be determined based on the passing position, and the focus adjustment signal may be provided to the second imaging apparatus when it is determined to adjust the focus of the second optical system.

In the above cell observation system and method, the first imaging apparatus may be a quantitative phase microscope. Further, the second imaging apparatus may be a quantitative phase microscope or a phase tomographic microscope. Further, the first imaging apparatus may be a quantitative phase microscope, and the second imaging apparatus may be a phase tomographic microscope.

In the above cell observation system, the control device may obtain the passing position based on the image by a phase difference autofocus technique, an image plane phase difference focus technique, or an autofocus technique using digital holography. Further, in the above cell observation method, in the focus adjustment instruction step, the passing position may be obtained based on the image by a phase difference autofocus technique, an image plane phase difference focus technique, or an autofocus technique using digital holography.

In the above cell observation system and method, the fluid may be caused to flow as a laminar flow in the flow path by using a hydrodynamic focusing effect.

INDUSTRIAL APPLICABILITY

The embodiments can be used as a cell observation system and a cell observation method capable of relaxing restriction of a flow speed of a cell due to a focusing speed.

REFERENCE SIGNS LIST

1—cell observation system, 10—flow path, 20—fluid, 30—cell, 40—first imaging apparatus, 41—first optical system, 42—first imaging element, 50—second imaging apparatus, 51—second optical system, 52—second imaging element, 60—control device, 70—analysis device, 100A-100D—imaging apparatus, 110—imaging optical system, 111—objective lens, 112—imaging lens, 120—imaging element, 130—light source, 140—irradiation optical system, 151—mirror, 152—beam splitter, 161—beam splitter, 162—mirror, 163—mirror, 164—beam splitter.

The invention claimed is:

1. A cell observation system for observing a cell moving in a flow path with a fluid, the system comprising:
   a first imaging apparatus including a first optical system and a first imaging element, and configured to capture an image of the cell by receiving, by the first imaging element, light reaching the first imaging element from the cell at a first position in a moving direction of the cell in the flow path through the first optical system;
   a second imaging apparatus including a second optical system, in which a focus is adjusted based on a focus adjustment signal, and a second imaging element, and configured to capture an image of the cell by receiving, by the second imaging element, light reaching the second imaging element from the cell at a second position downstream of the first position in the moving direction of the cell in the flow path through the second optical system; and
   a controller configured to obtain a passing position of the cell in a cross section of the flow path based on the image obtained by imaging by the first imaging element of the first imaging apparatus, and generate the focus adjustment signal based on the obtained passing position to provide the signal to the second optical system of the second imaging apparatus.

2. The cell observation system according to claim 1, wherein the controller is configured to determine whether to adjust the focus of the second optical system based on the passing position, and provide the focus adjustment signal to the second imaging apparatus when it is determined to adjust the focus of the second optical system.

3. The cell observation system according to claim 1, wherein the first imaging apparatus is a quantitative phase microscope.

4. The cell observation system according to claim 1, wherein the second imaging apparatus is a quantitative phase microscope or a phase tomographic microscope.

5. The cell observation system according to claim 1, wherein the first imaging apparatus is a quantitative phase microscope, and the second imaging apparatus is a phase tomographic microscope.

6. The cell observation system according to claim 1, wherein the controller is configured to obtain the passing position based on the image by a phase difference autofocus technique, an image plane phase difference focus technique, or an autofocus technique using digital holography.

7. The cell observation system according to claim 1, wherein the fluid is caused to flow as a laminar flow in the flow path by using a hydrodynamic focusing effect.

8. A cell observation method for observing a cell moving in a flow path with a fluid, the method comprising:
   performing a first imaging of, using a first imaging apparatus including a first optical system and a first imaging element, capturing an image of the cell by receiving, by the first imaging element, light reaching the first imaging element from the cell at a first position in a moving direction of the cell in the flow path through the first optical system;
   performing a second imaging of, using a second imaging apparatus including a second optical system, in which a focus is adjusted based on a focus adjustment signal, and a second imaging element, capturing an image of the cell by receiving, by the second imaging element, light reaching the second imaging element from the cell at a second position downstream of the first position in the moving direction of the cell in the flow path through the second optical system; and
   performing a focus adjustment instruction of, after the first imaging and before the second imaging, obtaining a passing position of the cell in a cross section of the flow path based on the image obtained by imaging by the first imaging element of the first imaging apparatus, and generating the focus adjustment signal based on the obtained passing position to provide the signal to the second optical system of the second imaging apparatus.

9. The cell observation method according to claim 8, wherein, in the focus adjustment instruction, whether to adjust the focus of the second optical system is determined based on the passing position, and the focus adjustment signal is provided to the second imaging apparatus when it is determined to adjust the focus of the second optical system.

10. The cell observation method according to claim 8, wherein a quantitative phase microscope is used as the first imaging apparatus.

11. The cell observation method according to claim 8, wherein a quantitative phase microscope or a phase tomographic microscope is used as the second imaging apparatus.

12. The cell observation method according to claim 8, wherein a quantitative phase microscope is used as the first imaging apparatus, and a phase tomographic microscope is used as the second imaging apparatus.

13. The cell observation method according to claim 8, wherein, in the focus adjustment instruction step, the passing position is obtained based on the image by a phase difference autofocus technique, an image plane phase difference focus technique, or an autofocus technique using digital holography.

14. The cell observation method according to claim 8, wherein the fluid is caused to flow as a laminar flow in the flow path by using a hydrodynamic focusing effect.

* * * * *